United States Patent [19]

Ismail et al.

[11] Patent Number: 5,185,247
[45] Date of Patent: Feb. 9, 1993

[54] STABILIZATION OF OXIDASE ENZYME-BASED TEST STRIPS

[75] Inventors: Ibrahim A. Ismail, South Bend; Wen H. Wu, Elkhart, both of Ind.

[73] Assignee: Miles Inc., Elkhart, Ind.

[21] Appl. No.: 841,073

[22] Filed: Feb. 25, 1992

Related U.S. Application Data

[62] Division of Ser. No. 321,724, Mar. 10, 1989, Pat. No. 5,116,729.

[51] Int. Cl.$^5$ ............ C12Q 1/26; C12Q 1/54; C12Q 1/00; C12N 9/96
[52] U.S. Cl. .................... 435/14; 435/10; 435/11; 435/25; 435/28
[58] Field of Search ............ 435/10, 11, 14, 25, 435/28

[56] References Cited

U.S. PATENT DOCUMENTS

4,220,713 9/1980 Rittersdorf ................ 435/14

FOREIGN PATENT DOCUMENTS

0009222 2/1980 European Pat. Off. .
0080304 1/1983 European Pat. Off. .
237325 5/1985 German Democratic Rep. .
57-68788 4/1982 Japan .
60-156386 8/1985 Japan .
61-15685 1/1986 Japan .

OTHER PUBLICATIONS

Kunst et al. pp. 178-185 in *Methods of Enzymatic Analysis* VI, ed. Bergmeyer.

*Primary Examiner*—Douglas W. Robinson
*Assistant Examiner*—Sandra Saucier
*Attorney, Agent, or Firm*—Roger N. Coe

[57] ABSTRACT

A method and composition for the enzymatic assay of a liquid test sample, such as urine or serum, for a specific analyte, such as glucose. The method utilizes a dry phase test strip comprising a carrier matrix impregnated with a stabilized enzyme reagent composition including an oxidase enzyme, such as glucose oxidase, that is capable of interacting with the analyte of interest; a chromogen that changes color in response to the analyte-oxidase enzyme interaction to reveal the presence and/or concentration of the analyte in the test sample; and a stabilizer, such as a hydrazide, like GIRARD'S Reagent T, or an amino acid, like arginine, or an amino acid derivative, like the tris(hydroxymethyl)aminomethane sale of glutamic acid, to improve the heat stability and shelf life of the dry phase test strip.

3 Claims, No Drawings

STABILIZATION OF OXIDASE ENZYME-BASED TEST STRIPS

This is a division of application Ser. No. 321,724, filed on Mar. 10, 1989, now U.S. Pat. No. 5,116,729.

FIELD OF THE INVENTION

The present invention relates to a composition and method of enzymatically assaying a test sample for the presence and concentration of a particular analyte. More particularly, the present invention relates to a new and improved method and composition for enzymatically assaying a liquid test sample, such as urine or serum, for analytes, such as glucose, uric acid, cholesterol or lower alcohols, like ethyl alcohol, by utilizing a dry phase test strip comprising a stabilized enzyme reagent composition incorporated into a carrier matrix. The present invention relates particularly to a new and improved composition and method for enzymatically assaying a liquid test sample for glucose. The stabilized enzyme reagent composition incorporated into the carrier matrix includes an oxidase enzyme capable of interacting with the analyte of interest; a chromogen that undergoes a color transition in response to the analyte-oxidase enzyme interaction to show the presence or the concentration of the analyte in the liquid test sample; and a stabilizer to improve the heat stability of the test strip, to improve the shelf life of the test strip and to more accurately detect and measure the analyte content of the liquid test sample. The stabilizer included in the stabilized enzyme reagent composition to unexpectedly improve the stability of the diagnostic test strip is a hydrazine based compound, such as a hydrazide, like GIRARD'S Reagent T, or an amino acid, such as arginine or lysine, or an amino acid derivative, such as the tris(hydroxymethyl)aminomethane salt of glutamic acid.

BACKGROUND OF THE INVENTION AND PRIOR ART

Dry phase test strips incorporating enzyme-based compositions are used extensively in clinical laboratories, physicians' offices, hospitals and in homes to assay urine or other liquid test samples for analytes such as glucose, cholesterol, lower alcohols and occult blood. The analyte test devices that measure fluctuations in a person's blood sugar, or glucose, levels are especially useful. In fact, these devices have become an every day necessity for many of the nation's several million diabetics Since diabetes can cause dangerous anomalies in blood chemistry and is believed to be a contributor to vision loss and kidney failure, most diabetics must test themselves periodically, then adjust their glucose count accordingly, usually with insulin injections. Patients who are insulin dependent, or about 10% to 15% of diabetics, must test their blood sugar levels as often as four times daily.

Therefore, the detection and quantitative determination of glucose in urine or serum is especially important for diabetic individuals who must control their diet in order to regulate sugar intake and who must be guided in this regard by frequent tests for blood and urine glucose. In addition, screening programs for diabetes depend on the availability of rapid, inexpensive and accurate methods of glucose determination.

Glucose is the sugar most commonly found in urine, although other sugars, such as lactose, fructose, galactose, and pentose, also can be found in the urine under certain conditions. The presence of detectable amounts of glucose in urine is known as glycosuria. Glycosuria occurs whenever the blood glucose level exceeds the reabsorption capacity, or renal threshold, of the renal tubules, that is, when the glomerular filtrate contains more glucose than the tubules are able to reabsorb. Since detectable amounts of glucose in the urine can be related to either a benign or a pathological condition, the physician must distinguish between these two possible conditions and, if necessary, begin medical treatment.

For example, renal glycosuria is observed even though blood glucose levels are normal because if the tubular reabsorption of glucose is below normal, some glucose will spill into the urine. This is a benign condition, as is the occurrence of glycosuria either after eating a heavy meal or during periods of emotional stress. In contrast, diabetes mellitus, the chief cause of glycosuria, is a pathological condition. This pathological condition leads to a noticeable elevation of blood glucose and, usually, to an increase in urine volume. Therefore, in clinical assays, the glucose content of the urine of a diabetic can reach levels as high as 10%, however, values of between 2% and 5% are more common.

As a result, in order to determine if an individual excretes an excess amount of glucose, and in order to monitor the effectiveness of a particular medical treatment, simple, accurate and inexpensive glucose detection assays have been developed. Furthermore, of the several different assay methods developed for the detection or measurement of glucose in urine and serum, the methods based on an enzymatic interaction between glucose oxidase and glucose have proven especially useful.

Testing for blood glucose at home became possible when reagent impregnated test strips for whole blood testing were developed. The reagent test strip includes a reagent composition comprising an enzyme, such as glucose oxidase, capable of catalyzing the oxidation reaction of glucose to gluconic acid and hydrogen peroxide; an oxidizable chromogenic indicator, such as an oxidizable dye, like o-tolidine; and a substance having peroxidative activity capable of catalyzing the oxidation of the indicator. The oxidizable dye or indicator turns a visually different shade of color depending upon the extent of oxidation. The extent of oxidation is in turn dependent upon the concentration of glucose in the blood sample.

The reactions occurring between the glucose and the reagent composition are represented as follows:

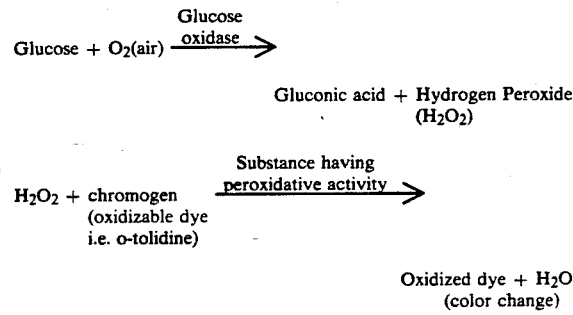

The reagent test strips generally include a carrier matrix such as a bibulous, e.g., cellulosic, material impregnated with the reagent composition capable of interacting with the glucose as described above.

For several years, diabetics have relied on commercially available urinalysis kits that, despite repeated improvements, have provided imprecise measurements of blood glucose. More recently, reagent test strips to test for glucose in urine were developed. Examples of early urine tests for glucose are described in U.S. Pat. Nos. 2,387,244 and 3,164,534. The most frequently used home urine assays for glucose are either the enzymatic assays based upon the interaction of glucose oxidase and glucose as discussed above or the reduction assays based upon the reduction of certain metal ions by glucose. The enzymatic glucose oxidase assay for glucose, as applied to urine, is specific for glucose. In this assay, like the blood assay, glucose oxidase catalyzes the oxidation of glucose to gluconic acid and hydrogen peroxide. The hydrogen peroxide, in the presence of peroxidase, oxidizes an indicator to produce a color change. Other sugars, such as lactose, fructose, galactose, and pentose are not substrates for glucose oxidase and, therefore, do not interact to cause an eventual color transition in the oxidizable indicator.

The urine glucose assay based on the reduction of metal ions, such as the cupric ion ($Cu^{++}$), is nonspecific for glucose. The reduction of the metal ion can result from interaction with any reducing substance present in the urine, such as creatinine, uric acid, ascorbic acid, or some other reducing sugar. The nonspecificity of the copper reduction assay is advantageous in that the assay detects sugars in the urine other than glucose. However, the assay has a disadvantage in that it detects other reducing substances in addition to sugars.

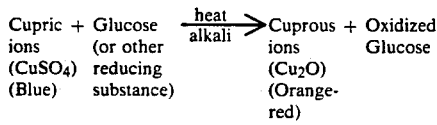

Some dry phase test strips used to assay for glucose have a single test area consisting of a small square pad of a carrier matrix impregnated with glucose oxidase, peroxidase and an oxidizable chromogenic indicator. Other dry phase test strips are multideterminant reagent strips that include one test area for the glucose assay as described above, and further include several additional test areas on the same strip to permit the simultaneous assay of other urinary constituents. For both types of colorimetric dry phase test strips, the assay for glucose in urine is performed simply by dipping the test strip into a well mixed, uncentrifuged urine sample, removing the excess urine by touching the side of the container, then comparing the resulting color of the test area of the test strip to a standardized color chart provided on the colorimetric test strip bottle. For example, in the copper reduction assay used to assay for the presence or concentration of glucose in a liquid test sample, the color resulting from the reaction with glucose is compared to a six-block color chart ranging from blue, indicating less than 0.1% concentration of glucose, to brown, indicating a 2.0% or greater glucose concentration. In accordance with the above-described method, an individual can readily determine, visually, the glucose content of a urine sample in the range of from about 0% to about 2%.

The most significant advantages of the present-day test strips are low cost, ease of use, relatively accurate assays and a short response time. These advantages make test strips ideal for the detection or measurement of glucose in urine by an individual at home. However, although a combination of glucose oxidase, peroxidase, and an oxidizable chromogenic indicator have been used extensively in glucose assays, several problems and disadvantages still exist in glucose assay methods utilizing enzymes. A continuing and significant problem troubling both the manufacturer and the user of the enzymatic test strip is the thermal instability of the enzymatic assay composition during the manufacture, shipment, storage and use of the dry phase test strip.

In order to determine the extent of the stability problem in regard to a particular enzyme composition, manufacturers routinely conduct stability studies at elevated temperatures. The results of these stability studies are used to predict the shelf life, and therefore the expiration date, of the dry phase test strip. Obviously, too short of a shelf life severely limits the viability of a test strip as a commercial product.

As discussed above, glucose test devices are used extensively both by trained medical personnel and by individuals in their own homes. Whereas the storage conditions in hospitals and clinical laboratories are usually relatively well controlled, storage conditions for home users can be extremely variable. In addition, home users may use several strips in a day and therefore consume a bottle of test strips in a short period, or they may use a test strip only relatively infrequently. Of course, the test strips also may be carried with the user and therefore be subject to a wide range of temperature conditions. This is particularly true of the glucose test strips that are used frequently by diabetics. However, the method and composition of the present invention provides improved thermal stability for enzymatic glucose assay compositions, for test strips utilizing a glucose oxidase/peroxidase composition, and for an enzymatic assay composition for other analytes, such that the dry phase test strip is more tolerant of varying manufacturing and storage conditions.

The stability of the test strip is a significant aspect in the commercial use of enzymatic test strips. An enzymatic test strip having a long shelf life can remain in distribution channels, such as in a manufacturer's and distributor's inventory, for long periods before shipment to a laboratory, and the laboratory can order a sufficiently large inventory of test strips so that frequent reordering is not necessary. Furthermore, increasingly critical cost factors are somewhat alleviated because fewer enzymatic test strips would have to be discarded after reaching an expiration date that is based on the shelf life stability of the test strips. As a result, it is important to provide a stable enzymatic test strip that a laboratory or home user will not have to return or discard before use.

Therefore, it would be extremely advantageous to have a simple, accurate and trustworthy method of assaying of urine or serum for glucose content without the disadvantage of unduly short test device shelf life. Such advantages are most evident in situations wherein an out-dated test device was used to assay urine for glucose and the instability of the enzyme reagent composition incorporated into the test device provided erroneous assay results, and hence to an erroneous diagnosis. By providing a stable dry phase test strip for the determination of the glucose concentration in urine or serum, in an easy to use form, such as a dip-and-read test strip, the urine or serum assay for glucose can be performed by laboratory personnel or by an individual at home to more precisely monitor the levels of glucose in urine or serum and/or the success of the medical treatment the individual is undergoing without the disadvantage of possibly using an out-dated and unreliable test strip.

As will be described more fully hereinafter, the method of the present invention allows the fast, accurate and trustworthy assay of urine or serum for glucose by utilizing a dry phase test strip that includes a stabilized enzyme-based reagent composition. The stabilized enzyme reagent composition improves the heat stability and shelf life of the dry phase test strip, thereby allowing the glucose concentration of test samples to be accurately determined using enzymatic test strips that either were manufactured in the relatively distant past or were stored at abnormally high temperatures.

As described previously, glycosuria is related to the precise nature of a clinical and pathological disorder and upon the severity of the specific disease. Glycosuria can be intermittent or continuous, with transient, intermittent glycosuria usually being caused by physiologic or functional conditions rather than by pathologic disorders. Therefore, accurate and trustworthy assays of urine and other test samples for glucose must be available for both laboratory and home use. The assays must permit the detection and measurement of glucose, such that a correct diagnosis can be made and correct medical treatment implemented, monitored and maintained.

Furthermore, any method of assaying for glucose in urine or other liquid test samples must yield accurate, trustworthy and reproducible results by utilizing a stable enzyme reagent composition that undergoes a color transition as a result of, and that can be correlated to, an interaction with the glucose content of the test sample. It is imperative that the assay reflects the true glucose concentration of the test sample and not an apparent, lower glucose concentration as a result of a reduction in the strength of the enzyme reagent composition over time. Additionally, the method and composition utilized in the assay for glucose should not adversely affect or interfere with the other test reagent pads that are present on multiple test pad strips.

Prior to the present invention, no known method of assaying urine or other liquid test samples for glucose included a stabilized enzyme reagent composition that so unexpectedly improved the stability of the dry phase test strip, thereby allowing accurate and trustworthy glucose assays to be made with relatively old and/or improperly stored test strips. In addition, although enzyme-based dry phase test strips have been used extensively in glucose assays for several years, no test strip has incorporated the enzyme reagent composition stabilizers utilized in the present invention to improve the stability of enzyme-based dry phase test strips.

The prior art contains numerous references relating to attempts to stabilize enzyme compositions incorporated into dry phase test strips. For example, Gruber et al, in U.S. Pat. No. 3,721,607, disclosed a stabilized test reagent for the enzymatic determination of glucose that includes both an inorganic azide and the compound 2,2'-azino-di-(3-ethylbenzothiazoline-6-sulfonic acid). However, the compositions disclosed by Gruber are stabilized solutions used in wet enzymatic assays for glucose and are not directed to stabilizing dry phase test strips used in an enzymatic assay for glucose. Similarly, Japanese Patent No. 55/013008 disclosed using lower alcohols to preserve glucose oxidase and/or peroxidase solutions.

European Patent No. 080,304 disclosed the use of an acidic amino acid to stabilize a reagent solution including an enzyme. Acidic amino acids, such as aminodicarboxylic acids and their ammonium and alkali metal salts, like glutamic acid, aspartic acid and o-aminoadipic acid, were used to stabilize an aqueous solution including enzyme, like glucose oxidase and choline oxidase. The European patent does not teach or suggest using any other amino acids or amino acid salts except for the acidic amino acids, and does not teach or suggest using the acidic amino acids as a stabilizer in enzymatic dry phase test strips.

U.S. Pat. No. 3,778,384 to Dooley disclosed the use of an arsenic compound in a glucose assay based on a glucose oxidase/peroxidase reagent composition. The arsenic compound, such as sodium arsenate, increases the sensitivity of enzyme reagent composition to glucose and increases the stability of the color transition occurring as a result of the glucose-enzyme interaction. Dooley also disclosed including thiourea in the composition to further stabilize the color transition. In contrast, the present invention is directed to stabilizing the enzyme reagent composition such that after prolonged storage, even under adverse storage conditions, the reagent composition has maintained its enzymatic and chemical activity and, therefore, the assay for glucose in urine or serum provides accurate and trustworthy results.

Green, in U.S. Pat. No. 4,189,536, disclosed using the tris(hydroxymethyl)aminomethane salt of 2-mercaptosuccinic acid as an activator or stabilizer in assays utilizing enzymes, like assays for creatine phosphokinase or glucose. However, similar to the compositions disclosed by Gruber in U.S. Pat. No. 3,721,607, the compounds disclosed by Green serve to stabilize the enzyme reagent first in the bulky dry storage phase and, then in the aqueous phase, after dissolution of the enzyme reagent, for improved performance of wet phase chemical assays. The compound disclosed by Green is used as a bulking agent and stabilizer for reagent compositions based upon the hexokinase catalyzed phosphorylation of glucose and the subsequent oxidation of glucose-6-phosphate, as opposed to an enzyme reagent stabilizer for the dry phase test strip assay of glucose based upon glucose oxidase and a peroxidase.

U.S. Pat. No. 4,220,713 to Rittersdorf et al disclosed the use of 1-arylsemicarbazides as stabilizers in test strips for colorimetric assays utilizing an oxidizable indicator, such as a glucose assay based on glucose oxidase and peroxidase. The parent compound, semicarbazide, specifically is described as being nonfunctional as a stabilizer. In contrast, the method and composition of the present invention is directed to various hydrazides and to certain amino acids and amino acid derivatives that stabilize enzymatic test strips used to assay for analytes.

Motobayashi, in U.S. Pat. No. 4,386,053, disclosed a stabilizer for an occult blood assay device that incorporates an organic peroxide, a chromogen and a buffer. The stabilizer is an aromatic compound having a substituted phenyl moiety and a substituted amide or substituted sulfonamide moiety. Similarly, European Patent No. 071,730 to Klose disclosed a stabilized reagent mixture for the detection of hydrogen peroxide or hydrogen peroxide-forming systems including methylbenzothiazolone hydrazone, an oxidizable aromatic amine and a ferrocyanide, azide or chelating agent as a stabilizer.

In contrast to the prior art, and in contrast to presently available commercial test strips, the method and composition of the present invention provides increased stability to dry phase enzymatic test strips used in the detection and measurement of glucose and other analytes in urine and serum by utilizing a hydrazide stabilizer or an amino acid stabilizer or an amino acid derivative stabilizer. Unexpectedly improved stability of the enzyme reagent composition results when both a hydrazide and an amino acid, or both a hydrazide and an amino acid derivative, is utilized as the stabilizer of the enzyme reagent composition. Hence, in accordance with the method and composition of the present invention, new and unexpected results are achieved in stabilizing dry phase enzymatic test strips used to assay urine and other liquid test samples for analytes, such as glucose and cholesterol, by incorporating a hydrazide stabilized or an amino acid stabilized or an amino acid derivative stabilized enzyme reagent composition into a carrier matrix.

SUMMARY OF THE INVENTION

In brief, the present invention is directed to a composition and method of enzymatically assaying urine or serum for the presence and/or concentration of analytes such as glucose, cholesterol, uric acid and lower alcohols. The assay is performed with a dry phase test strip that includes a carrier matrix impregnated with a stabilized enzyme reagent composition capable of interacting with an analyte present in the test sample to produce a detectable response. For home use, the stabilized enzyme reagent composition produces a visually detectable response. For laboratory use, the stabilized enzyme reagent composition produces a response that is detectable visually or by instrument. The carrier matrix of the dry phase test strip comprises a bibulous material, such as filter paper, or a nonbibulous material, such as a permeable polymeric strip, layer or membrane.

It has been demonstrated that incorporating a hydrazide or an amino acid or an amino acid derivative into an enzyme reagent composition, such as the glucose oxidase, peroxidase and oxidizable indicator composition used to assay for glucose, stabilizes the enzyme reagent composition and therefore protects the test strip and extends the useful life of the test strip. By including the stabilized enzyme reagent composition of the present invention in an enzymatic clinical test method, the presence and semiquantitative concentration of an analyte in a urine or serum sample can be accurately and reliably determined by the intensity of the color change of a test strip. In accordance with an important feature of the present invention, the possibility of having used a test strip that has lost either all or a significant amount of its enzymatic activity during storage, and therefore yielding incorrect and misleading assay results, has been diminished or eliminated by using the stabilized enzyme reagent composition.

More particularly, the present invention is directed to a method of enzymatically assaying urine or other test samples for analytes by utilizing a new and improved stabilized enzyme reagent composition. It has been demonstrated that employing a hydrazide or an amino acid or an amino acid derivative in an enzyme-based reagent composition provides dry phase test strips of improved stability, and therefore provides increased reliability in the assay results.

In accordance with another important feature of the present invention, dry phase test strips employing an enzyme reagent composition demonstrate an increased stability and shelf life of from about three to about five times the shelf life of present day test strips. By utilizing the stabilized enzyme reagent composition of the present invention in clinical test methods, the qualitative and/or semiquantitative concentration of analytes, such as glucose, in urine or other liquid test samples can be more accurately and more reliably determined because the test strip stability provided by the addition of the hydrazide or the amino acid or the amino acid derivative increases the clinically useful life of the test strip by maintaining the high chemical and enzymatic activity of the enzyme reagent composition over long and/or adverse storage conditions.

Therefore, it is an object of the present invention to provide a simple, trustworthy, accurate and reproducible method of enzymatically assaying urine or other liquid test samples for analytes.

It is also an object of the present invention to provide a method of enzymatically assaying urine or other liquid test samples with a dry phase test strip that maintains its enzymatic and chemical activity over long periods of time and at increased temperatures.

Another object of the present invention is to provide a method of enzymatically assaying urine or other liquid test samples by utilizing a stabilized enzyme reagent composition.

Another object of the present invention is to provide a method of enzymatically assaying urine or other liquid test samples by utilizing a stabilized enzyme reagent composition that can interact with an analyte and undergo a detectable and measurable color transition to establish the presence and concentration of the analyte in the test sample.

Another object of the present invention is to provide a stabilized enzyme reagent composition that can interact with an analyte and undergo a visually and/or instrumentally differentiable color transition to allow the reliable semiquantitative determination of the concentration of the analyte in the urine or other liquid test sample.

Another object of the present invention to provide a method of enzymatically assaying urine or serum for glucose.

Another object of the present invention is to provide a method of enzymatically assaying for glucose in urine or serum that does not interfere with or provide erroneous results in simultaneous urine or serum assays for analytes other than glucose.

Another object of the present invention is to provide a stabilized enzyme reagent composition that maintains its enzymatic and chemical activity over time and at increased temperatures, and that can interact with glucose to undergo a detectable color transition to establish the presence or concentration of glucose in urine or serum.

Another object of the present invention is to provide a stabilized enzyme reagent composition that can interact with glucose and undergo a visually or instrumentally differentiable color transition to allow the semiquantitative determination of the concentration of glucose in the urine or serum.

Another object of the present invention is to provide a stabilized enzyme reagent composition for the detection and/or semiquantitative measurement of glucose in a liquid sample that includes glucose oxidase, a peroxidase, an oxidizable chromogenic indicator, and a stabilizer such that the enzyme reagent composition maintains its enzymatic and chemical activity over long periods of time and at relatively high temperatures.

Another object of the present invention is to provide a stabilized enzyme reagent composition, including a hydrazide stabilizer or an amino acid stabilizer or an amino acid derivative stabilizer, for incorporation into a dry phase test strip to assay urine and other liquid test samples for analytes.

Another object of the present invention is to provide a stabilized enzyme reagent composition for incorporation into a dry phase test strip to assay urine and other liquid test samples for analytes, wherein the stabilized enzyme reagent composition comprises glucose oxidase; a peroxidase; an oxidizable chromogenic indicator; a buffer; and a stabilizer, such as a hydrazide, like hydrazine monohydrate, (carboxymethyl)trimethylammonium chloride hydrazide, 1-(carboxymethyl)-pyridinium chloride hydrazide, 2-hydrazine2-imidazoline hydrobromide or 2-furoic acid hydrazide; or an amino acid, like arginine or lysine; or an amino acid derivative, like the tris(hydroxymethyl)aminomethane salt of an amino acid, such as the tris(hydroxymethyl)aminomethane salt of glutamic acid.

The above and other objects and advantages of the present invention will become apparent from the following detailed description of the invention.

DETAILED DESCRIPTION OF THE INVENTION

In accordance with the method and composition of the present invention, the presence or amount of an analyte, such as glucose, in a liquid test sample, such as urine or serum, can be determined by an interaction between a stabilized enzyme reagent composition and the analyte of interest to cause a detectable or measurable change in a chromogenic indicator. Normally the enzyme used is an oxidase, such as glucose oxidase, and the resulting enzyme-analyte interaction causes a color transition in an oxidizable chromogenic indicator such as o-toluidine, o-dianisidine or 3,3',5,5'-tetramethylbenzidine.

One inherent disadvantage in enzymatic assays incorporating an oxidizable chromogenic indicator is that the indicator must be oxidized relatively easily in order to obtain a facile and relatively rapid color transition to demonstrate the presence or concentration of the analyte. However, because the indicator is so easily oxidized, the indicator is therefore susceptible to oxidation by atmospheric oxygen, especially in the presence of atmospheric moisture and light. Therefore, the inherent stability of the chromogenic indicator chosen for incorporation into the enzyme reagent composition must be considered. The instability of the enzyme/oxidizable indicator-based assay procedure is further aggravated by long storage periods, by relatively high temperatures, and by general mishandling of the test strip by lay persons using the test strip for home testing for an analyte.

Therefore, the method of the present invention is directed to a stabilized enzyme reagent composition that can be incorporated into a dry phase test strip for the assay of analytes in a liquid test sample. It has been found that the addition of a hydrazide or an amino acid or an amino acid derivative to the oxidase enzyme and oxidizable indicator reagent composition effectively protects the enzyme reagent composition from the adverse affects of atmospheric oxygen, atmospheric moisture and light to enable the dry phase test strip to be stored for long periods of time, even at relatively high temperatures, without an unacceptable loss in enzymatic or chemical activity. Furthermore, although the hydrazide or amino acid or amino acid derivative act to stabilize the enzyme reagent composition, these stabilizers do not retard the enzyme-analyte interaction and resulting indicator color transition, therefore still allowing sufficiently rapid analyte assays to be made. In addition, the resulting analyte assay is reliable, accurate and trustworthy because the stabilized enzyme reagent composition has sufficiently maintained its enzymatic and chemical activity over time. It has been found that the test strips including the stabilized enzyme reagent composition have a longer clinically useful life, thereby avoiding the necessity of having to discard unused test strips after a relatively short storage period.

From the following detailed description of the invention, it will become apparent that, in addition to assaying urine, the method and composition of the present invention also can be used to determine the presence and semiquantitative concentration of an analyte in blood plasma and serums; and more generally, the analyte content of many other analyte containing fluids as well. For example, sweat is an ultrafiltrate of blood and has a low, variable glucose concentration. The literature indicates that glucose concentration in the interstitial extracellular space and intramuscular or subcutaneous locations is lower than blood glucose, but this glucose concentration is believed to be a good measure of the blood glucose. Thus, glucose reaches the underside of the skin in potentially sufficient amounts for detection and measurement.

In accordance with another important feature of the present invention, the method and composition of the present invention can be employed either in dry phase, test pad assays to determine the presence or semiquantitative concentration of an analyte in urine or serum or in aqueous, liquid phase assays. Dry phase enzymatic reagent test strips have the benefits of low cost and convenience but suffer from a relatively short clinically useful life. Therefore, a longer "shelf-life", or storage life, for the enzymatic test strip would enable the manufacturer to prepare and store a larger number of the test strips more efficiently, and thus help to keep the cost of the test strip as low as possible by avoiding the need to discard out-dated, unsold test strips. Surprisingly and unexpectedly, a variety of, but not all, hydrazides, amino acids and amino acid derivatives have demonstrated the ability to stabilize enzyme reagent compositions that interact with an analyte and undergo a detectable color change to show the presence and/or amount of the analyte in a liquid test sample.

The stability of a dry phase reagent test strip is determined by storing the test strip for a designated time period at a given temperature, and then determining the reactivity of the test strip against known standards. Since many reagent test strips are used by comparing the color of the reacted test strip to a color chart prepared by the manufacturer for the user, the stability data often is reported by referring to this color chart. For example, after storing a particular test strip at room temperature for ten weeks, it may be reported that one-half of a color block of reactivity is lost. As used here, and hereinafter, a color block is defined as the color difference between consecutive glucose levels. Stability data often is obtained by elevating the temperature to increase the stress on the test strip, storing the test strip at the elevated temperature for a short period of time, then empirically correlating these increased temperature results to an expected shelf life at room temperature. As discussed previously, thermal instability has been the principal problem facing enzymatic reagent test strips, such as test strips used for glucose determinations based on glucose oxidase and peroxidase reactions. However, as will be demonstrated hereinafter in the detailed description of the invention, the thermal instability problem has been reduced or eliminated by the addition of certain hydrazides or certain amino acids or certain amino acid derivatives to an oxidase enzyme-based reagent composition.

In the normal manufacture of a dry phase test strip, the components comprising the enzyme reagent composition are solubilized; then impregnated into a carrier matrix, such as filter paper; and the impregnated carrier matrix then is dried at an elevated temperature. Some of the components of an enzyme reagent composition, such as the enzymes, can be partially or totally inactivated by heat applied during the manufacture of the test strip, or can be partially or totally inactivated if the dry phase test strip is stored at an elevated temperature. In accordance with the composition and method of the present invention, the problem of thermal inactivation, and the problem of test strip inactivation due to long storage times, have been alleviated or eliminated by including a hydrazide or an amino acid or amino acid derivative in the enzyme reagent composition, thereby providing a dry phase test strip having enhanced stability under heat stress at 60° C.

As previously discussed, due to their inherent nature, the oxidizable indicators used in the enzyme reagent composition are easily oxidizable substances. Therefore, it is expected that they are oxidized to varying extents by air, especially when exposed to light. As a result, several potentially useful oxidizable indicators are not used in enzymatic test strips because the storage stability of the oxidizable indicator is very limited. Therefore, several investigators sought appropriate stabilizers for these oxidizable indicators such that they could be used in enzyme-based test strips. In addition, the stabilizer must, in turn, be sufficiently stable itself and must not appreciably alter the sensitivity or the accuracy of the test strip, such as by deactivating the enzymes. In contrast, the method and composition of the present invention is directed to stabilization of the enzyme component of the enzyme reagent composition and to stabilization of the dry phase test strip as opposed to stabilization of the oxidizable dye or stabilization of the color formed as a result of the enzyme-analyte interaction.

In general, an enzyme or enzyme solution can be stabilized either by changing the solvent nature of the liquid media, by binding the enzyme to either high molecular weight or low molecular weight compounds in order to enhance the structural stability of the enzyme and/or by adding bacteriocides to prevent the growth of microorganisms in liquid media and, therefore, prevent the degradation of enzyme molecules.

The prior art has shown that certain amino compounds have been used to inhibit the degradation of glucose oxidase. It has been theorized that the inhibition of enzyme degradation arises because of the binding of the amino inhibitor to the enzyme, thereby resulting in stabilization of the enzyme. As also disclosed in the prior art, other classes of chemical compounds have been used to stabilize enzymes or enzyme solutions, however, these compounds served either simply as bulking agents, as indicator stabilizers or as bacteriocides. As will be discussed more completely hereinafter, in accordance with the method and composition of the present invention, the hydrazide or amino acid or amino acid derivative included in the enzyme reagent composition serve to stabilize the enzyme, as opposed to stabilizing the indicator dye.

In the normal production of a dry phase test strip for glucose, the test strip is successively impregnated with two solutions. The first impregnation solution includes the test reagents required for the assay of glucose in the test sample. The second impregnation solution includes reagents required to minimize or eliminate ascorbate interference with the glucose assay. The hydrazide, amino acid or amino acid derivative, such as the tris(hydroxymethyl)aminomethane salt of glutamic acid, or TRIS glutamate, that provides improved stabilization of the enzyme reagent composition and, therefore the test strip, usually is present in the first impregnation solution as demonstrated in Example 1.

EXAMPLE 1

Stabilized Enzyme Reagent Composition (First Impregnation Solution)

| | |
|---|---|
| 3,3',5,5'-Tetramethyl-benzidine (TMB) | 19 mM |
| Monoethyl ester of poly(methyl vinyl ether/maleic acid) (50% in ethanol) | 3% |
| Polyvinylpyrrolidone polymer (MW 10,000 to 700,000) | 1.4% |
| Sodium Lauryl Sarcosinate (30% aqueous) | 0.3% |
| TRIS glutamate | 200 mM |
| Succinate buffer (to pH 4.5-6.0) | 250 mM |
| Glucose oxidase | 112 U/mL |
| Peroxidase | 245 U/mL |
| Acetone | 30% Final |
| Water | q.s. to 100% |

As used above, and throughout this specification, the abbreviations used in the specification are defined as:

| | |
|---|---|
| mg | milligrams |
| mL | milliliters |
| M | molar (moles per liter) |
| mM | millimolar (millimoles per liter) |
| U | units (International units defined as enzyme activity that will catalyze the reaction of one micromole of substrat per minute under specified reaction conditions). |

The components of the stabilized enzyme reagent composition of Example 1 include a 30% (by weight) aqueous solution of the surfactant sodium lauryl sarcosinate, commercially available under the tradenames of SARKOSYL NL-30, CIBA-Geigy Corp., Greensboro, N.C.; HAMPOSYL L-30, W. R. Grace Co., Lexington, Mass.; MAPROSYL 30, Stepan Co., Northfield, Ill.; and SARKOSINE LD, American Hoechst, Somerville, N.J. Other components included in Example 1 are a 45% (by weight) aqueous solution of a polyvinylpyrrolidone polymer (MW 220,000), commercially available under the tradename of PVP K60, GAF Corp., N.Y., N.Y.; and a 50% ethanol solution of the monoethyl ester of a poly(methyl vinyl ether/maleic anhydride), commercially available under the tradename GANTREZ ES225, GAF Corp., N.Y., N.Y. TRIS glutamate is the tris(hydroxymethyl)aminomethane salt of glutamic acid. The pH of this first impregnation solution is adjusted to, and buffered at, a pH of between about 4.5 and about 6.0, however, the preferred pH range is between about 5.4 and about 5.7. Acetone is the solvent used in the stabilized enzyme reagent composition of Example 1, however, other organic solvents such as methoxypropanol or lower alcohols, like ethanol, also can be used. The TMB indicator, glucose oxidase and peroxidase are the enzyme and indicator components that interact with the glucose in the test sample, or undergo or cause another composition component to undergo a color transition in response to the glucose interaction.

The second impregnation solution, necessary to minimize or eliminate ascorbate interference, is exemplified by the composition of Example 2.

EXAMPLE 2

Ascorbate Interference Composition (Second Impregnation Solution)

| | |
|---|---|
| Mercuric Oxide | 100 mM |
| Sarcosine | 400 mM |
| Polyvinylpyrrolidone polymer (MW 10,000 to 700,000) | 4% |
| Polyethoxylated(20)oleyl alcohol | 0.06% |
| Isopropyl Alcohol | 15% |
| Water | q.s. to 100% |

Sarcosine is N-methylglycine, available from Aldrich Chemical Co., Milwaukee, Wis. The polyvinylpyrrolidone polymer is identical to the polymer used in Example 1. The emulsifier, polyethoxylated(20)oleyl alcohol, is available commercially under the tradename EMULPHOR ON-870 from GAF Corp., N.Y., N.Y. However, other nonionic and inert emulsifiers having an HLB value (hydrophilic-lipophilic balance) approximating the HLB value of polyethoxylated(20)oleyl alcohol, such as nonionic emulsifiers having an HLB of from about 14 to about 17, also can be used in the second impregnation solution of Example 2. The isopropyl alcohol is used as a solvent and, in addition, other organic solvents, such as methoxypropanol, acetone, or ethanol, or mixtures thereof, also can be used.

The dry phase test strips were prepared by first impregnating a carrier matrix, such as filter paper or a permeable polymeric film with the first impregnation solution of Example 1. After drying the impregnated carrier matrix at 60° C. for 20 minutes, the impregnated carrier matrix then is impregnated with the second impregnation solution of Example 2, and then dried again at 60° C. for 20 minutes. The dried and twice impregnated carrier matrix then was slit into 1/5"×1/5" pads. The pads of carrier matrix impregnated by the solutions of Example 1 and Example 2 were secured onto the tip of a plastic handle by a double sided adhesive.

To demonstrate the increased thermal stability of a test strip incorporating an enzyme reagent composition including an amino acid or amino acid derivative, test strips incorporating the impregnation solutions of Examples 1 and 2 were manufactured by the above process and compared to control test strips identically prepared except that the first impregnation solution incorporated into the control test strips did not include the TRIS glutamate stabilizer. The two sets of test strips were compared by dipping the test strips into standardized urine solutions having glucose concentrations of negative, 30, 100, 250, 500, 1000 and 3000 mg/dL, then examining the test strips for the degree and/or intensity of a color transition. It was found that the control test strip, wherein the TRIS glutamate was omitted, was highly unstable to heat stress. For example, after storage at 60° C. for 3 days, the standardized urine solution containing 30 mg/dL of glucose gave a negative glucose reading and the standardized urine solution containing 100 mg/dL of glucose gave a trace glucose reading. However, upon incorporating 200 mM of TRIS glutamate into the enzyme reagent composition, as in Example 1, the test strips retained more than 90% of their initial activity after 3 days storage at 60° C. in assays of all the standardized urine solutions containing from 30 mg/dL to 3000 mg/dL glucose.

In order to show that the amino acid derivative, TRIS glutamate, is the component that provides the increased stability to the enzymatic test strip, an experiment was performed to demonstrate the effect of removing various other components from the stabilized enzyme reagent composition of Example 1 upon test strip stability. For apparent reasons, the solvent cannot be removed, or substituted for, because it is required to solubilize the enzyme reagent composition components. Similarly, the TMB oxidizable indicator, the glucose oxidase and the peroxidase cannot be removed from the enzyme reagent composition as these components are the essential ingredients for performing the glucose assay. Likewise, the buffer cannot be eliminated because it is necessary in order to perform a reliable glucose assay. However, it was found that removal of the sodium lauryl sarcosinate, the polyvinylpyrrolidone polymer, or the monoethyl ester of poly(methyl vinyl ether/maleic acid) from the enzyme reagent composition of Example 1 did not adversely affect the stability of the enzymatic test strips including TRIS glutamate, thereby demonstrating that the TRIS glutamate was the composition component responsible for the increased stability of the test strip. In general, the sarcosinate and the two polymers are included in the enzyme reagent composition of Example 1 to take advantage of their surface active, leveling, film forming, dispersing, and dye stabilizing properties and dye solubilizing properties, both during the manufacture of test strips and when using the test strips to perform an analyte assay.

As will be discussed more fully hereinafter, other amino acids and amino acid derivatives, especially when used in combination with a hydrazide, also serve to increase the stability of the dry phase enzymatic test strips. Furthermore, in accordance with another important feature of the present invention, it has been found that the addition of a hydrazide chosen from the group consisting of (carboxymethyl)trimethylammonium chloride hydrazide, 1-(carboxymethyl)pyridinium chloride hydrazide, hydrazine monohydrate, 2-hydrazine-2-imidazoline hydrobromide or 2-furoic acid hydrazide, or combinations thereof, stabilizes and protects the enzyme reagent compositions against a significant loss in enzymatic and chemical activity due to heat stress and/or prolonged storage. The preferred hydrazides include (carboxymethyl)trimethylammonium chloride hydrazide, 1-(carboxymethyl)pyridinium chloride hydrazide and hydrazine monohydrate. The hydrazide, (carboxymethyl)trimethylammonium chloride hydrazine, available commercially as GIRARD'S REAGENT T from Aldrich Chemical Company, Inc., Milwaukee, Wis., is especially preferred.

It is known that the instability of dry phase test strips incorporating enzyme reagent compositions can be attributed either to thermal or chemical deactivation of the enzyme or enzymes or to physical changes occurring within the test strip that reduce the effectiveness of the enzyme activity. It has been theorized that a test strip incorporating an enzyme reagent composition including TRIS glutamate, as described above, may stabilize the enzymatic test strip by preventing physical changes from occurring within the strip. Furthermore, it has been theorized that a hydrazide present in the enzyme reagent composition may stabilize the enzymatic test strip by binding with the enzyme to form a stable enzyme-hydrazide complex. The semicarbazide stabilizer described in Rittersdorf et al U.S. Pat. No. 4,220,713, although similar in structure to the hydrazides disclosed in the present invention, performs an entirely different function from hydrazide disclosed herein in regard to stabilizing the enzymatic test strip The sole purpose of adding the semicarbazides disclosed in U.S. Pat. No. 4,220,173 to the enzyme reagent composition is to prevent premature oxidation of the oxidizable indicator present in the test strip by atmospheric oxygen. The particular stabilizers disclosed in U.S. Pat. No. 4,220,173 are antioxidants, with the parent material, semicarbazide, specifically disclosed as being unsuitable as a stabilizer. The Rittersdorf et al patent teaches that only a specific class of semicarbazides, having the structure Ar—NHNH—CO—NH$_2$, provided sufficient stabilization to the test strip. The hydrazide compounds of the present invention were not disclosed or suggested in this prior art patent as being enzyme stabilizers for enzyme reagent compositions incorporated into dry phase test strips.

In accordance with the method of the present invention, certain hydrazide compounds, having the structure R—NHNH$_2$, significantly improve the stability of enzymatic test strips. The hydrazide moiety (—NHNH$_2$) is essential in regard to improving the stability of the test strip, and the degree of increased stability is dependent upon the nature of R group. It has been found that hydrazides either having a hydrogen as the R group or having a positively charged quaternary ammonium moiety present in the R group are the most effective stabilizers; and hydrazides having heterocyclic moieties present in the R group demonstrate varying degrees of effectiveness. Furthermore, hydrazides having negatively charged moieties or having phenyl moieties present in the R group demonstrate a strong destabilizing effects.

As described above, an enzyme reagent composition used to assay for glucose includes glucose oxidase, peroxidase and an oxidizable chromogenic indicator incorporated into a carrier matrix, such as filter paper. A variety of buffers or combinations of buffers capable of providing a pH of from about 4 to about 7 can be included in the enzyme reagent composition to allow the assay of body fluids. For example, a succinate buffer, capable of maintaining a pH range of from about 4.7 to about 5.7 is preferred for a urine glucose assay designed for visual testing, however, other suitable buffers also are available and well known to those skilled in the art of designing test kits.

In addition, other components can be included in the enzyme reagent composition to provide a more stable commercial composition for use in a dry phase test strip, e.g., polymers such as polyvinylpyrrolidone and poly(methyl vinyl ether/maleic acid) to improve the uniformity of color development and to improve color stability, or a glutamate salt, most preferably tris(hydroxymethyl)aminomethane glutamate to increase the stability of the test strip Other components such as surfactants or background dyes can be included in the enzyme reagent composition to further improve the uniformity of color development and to improve color differentiation between the test strip before and after contacting the test sample. For example, additional inert dyes often are added to the enzyme reagent composition to alleviate the problem of discoloration of the reagent test pad by a urine sample, that, in turn, could interfere with a visual determination of the color change.

As previously described, the enzyme reagent composition is incorporated into a carrier matrix, then the reagent-containing matrix is dried to provide a dry phase test strip. The carrier matrix can be any substance capable of incorporating the components of the enzyme reagent composition. However, the carrier matrix must be substantially inert with respect to the enzyme reagent composition, and must be porous and/or absorbent relative to the liquid sample to be tested. The expression "carrier matrix" refers to either bibulous matrices or nonbibulous matrices that are insoluble in, and maintain their structural integrity when exposed to, water or physiological fluids. Suitable bibulous matrices that are useful in the method of the present invention include, but are not limited to, paper, sponge materials, cellulose, hydrophilic inorganic powders, wood, synthetic resin fleeces, woven and nonwoven fabrics and like materials. Nonlimiting examples of nonbibulous matrices include glass fiber, permeable polymer films and preformed or microporous membranes.

Typically, the dry phase test strip, designed either as a single pad test strip (to assay only for a single analyte) or as a multiple pad test strip (to assay for several urine or serum analytes simultaneously), includes a support strip, or handle, normally constructed from a hydrophobic plastic; and a reagent test pad, including the carrier matrix impregnated with the chemical reagents required to perform the assay of interest. The handle normally is formed from materials such as cellulose acetate, polyethylene, terephthalate, polycarbonate or polystyrene. The carrier matrix is constructed most advantageously from filter paper or a permeable polymeric film.

Incorporation of the chemical reagents into the carrier matrix can be accomplished by any method such as dipping, spreading or spraying. A preferred method is to impregnate a carrier matrix, such as filter paper, by dipping the carrier matrix into a reagent solution, then drying the impregnated carrier matrix to remove the solvent. Drying can be accomplished by any method that does not deleteriously affect the reagents incorporated into the carrier matrix. The usual drying method is by means of an air oven.

In accordance with another important feature of the present invention, various hydrazide compounds can be included in an enzyme reagent composition, either alone or in combination with an amino acid or an amino acid derivative. Subsequent incorporation of the enzyme reagent composition including the hydrazide, amino acid, or amino acid derivative into a carrier matrix increases the thermal stability and the shelf life of the resulting enzymatic test strip. For example, the enzyme reagent composition of Example 3 was used to test various hydrazides for their ability to stabilize dry phase enzymatic test strips. The composition of Example 2 also was impregnated into the carrier matrix in order to eliminate any ascorbate interferences with the urine assay. The composition of Example 3 and the composition of Example 2 were impregnated into a carrier matrix according to the following procedure to give a stabilized enzymatic test strip useful in the assay of glucose.

A carrier matrix comprising WHATMAN 54 filter paper, available commercially from Whatman Ltd., Maidstone, Kent, U.K., was dipped into an enzyme reagent composition of Example 3:

EXAMPLE 3

Enzyme Reagent Compositions Containing Hydrazides

| | |
|---|---|
| 3,3',5,5'-Tetramethyl-benzidine (121 mg/mL in acetone) | 1.5 mL |
| Acetone | 1.12 mL |
| GANTREZ ES-225 (20% in acetone) | 1.50 mL |
| Succinic Acid (1M, pH 5.3) | 1.5 mL |
| Polyvinylpyrrolidone (PVP K60) (20% in water) | 1.50 mL |
| Ascorbic Acid (10%) | 0.03 mL |
| Sodium Lauryl Sarcosinate (30% in water) | 0.03 mL |
| Polyethoxylated(20) oleyl alcohol (10% in water) | 0.20 mL |
| TRIS glutamate (2M) | 1.00 mL |
| Hydrazide (250 mM) | 1.00 mL |
| Glucose Oxidase (5000 U/mL) | 0.15 mL |
| *-continued* | |
| Peroxidase (5000 U/mL) | 0.50 mL |

After drying the impregnated carrier matrix for 15 minutes at 60° C., the impregnated carrier matrix then was dipped into the composition of Example 2 in order to impart to ascorbate interference resistance to the test strip. The use of a mercury oxide-sarcosine complex to impart ascorbate resistance, as exemplified by the ascorbate interference composition of Example 2, is fully disclosed in U.S. Pat. No. 4,288,541. The twice-impregnated carrier matrix again was dried at 60° C. for 15 minutes.

The carrier matrix incorporating the enzyme reagent composition and the ascorbate interference composition then was cut into 1/5" squares and secured to the tip of a plastic handle with double-sided adhesive. The enzymatic test strips were heat stressed at 60° C. for 3 days. The activity of the heat stressed test strips then was compared to the reactivity of heat stressed control test strips impregnated with the enzyme reagent composition of Example 3 absent the hydrazide stabilizer.

TABLE I below lists the various hydrazides that were included in the enzyme reagent composition of Example 3 and tested for their relative effectiveness in stabilizing the chemical and enzymatic activity of an enzymatic test strip. In TABLE I, the expression "very effective" is defined to mean a strong stabilizing effect compared to the control test strip containing no hydrazide; the expression "effective" is defined to mean a net stabilizing effect; the expression "no effect" is defined to mean that neither stabilization nor destabilization was observed; and the expression "strongly destabilizing" is defined to mean a destabilizing effect.

TABLE I

| Hydrazide | Structure | Relative Effectiveness |
|---|---|---|
| (Carboxymethyl)trimethylammonium chloride hydrazide (GIRARD'S Reagent T) | $(CH_3)_3N^+—CH_2—\underset{\underset{O}{\|}}{C}—NH—NH_2$ | very effective |
| 1-(Carboxymethyl)pyridinium chloride hydrazide (GIRARD'S Reagent P) | 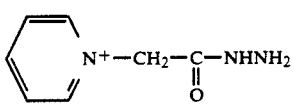 | very effective |
| Hydrazine monohydrate | $H_2N—NH_2.H_2O$ | very effective |
| 2-Hydrazine-2-imidazoline hydrobromide | 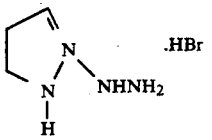 | effective |
| 2-Furoic acid hydrazide | 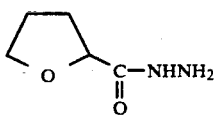 | effective |
| Semicarbazide | 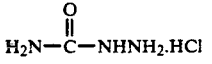 | no effect |

TABLE I-continued

| Hydrazide | Structure | Relative Effectiveness |
|---|---|---|
| Isonicotinic acid hydrazide | (pyridine ring)—C(=O)—NHNH$_2$ | no effect |
| 2-Hydroxy-ethylhydrazine | HO—CH$_2$CH$_2$—NHNH$_2$ | no effect |
| p-Toluene sulfonhydrazide | CH$_3$—C$_6$H$_4$—S(=O)$_2$—NHNH$_2$ | no effect |
| 4-Hydrazinobenzoic acid | HOOC—C$_6$H$_4$—NHNH$_2$ | no effect |
| Phenelzine | C$_6$H$_5$—CH$_2$CH$_2$—NHNH$_2$ | strong destabilizing |
| 4-methoxy-phenylhydrazine | CH$_3$O—C$_6$H$_4$—NHNH$_2$·HCl | strong destabilizing |

As will be discussed more fully hereinafter, analogous to proving the stabilizing effect afforded by including an amino acid or an amino acid derivative in the enzyme reagent composition, tests were performed that identified the hydrazide component of the enzyme reagent composition of Example 3 as the stabilizer component of the enzyme composition even in the absence of other enzyme reagent composition components, such as the poly(methyl vinyl ethyl/maleic acid) ester, the polyvinylpyrrolidone, or the TRIS glutamate To show that certain hydrazides improve the heat stability and prolong the shelf life of dry phase enzymatic test strips even in the absence of TRIS glutamate, two sets of dry phase enzymatic test strips were prepared as described above and using the compositions of Example 3 and Example 2. One set of test strips was impregnated with an enzyme reagent composition of Example 3 including the TRIS glutamate, and the other set of test strips was impregnated with an enzyme reagent composition of Example 3 excluding the TRIS glutamate. Within each set of dry enzymatic test strips were two subsets of test strips prepared by including 0 mM and 25 mM of the hydrazide, GIRARD'S Reagent T, in the enzyme reagent composition. In general, after subjecting the test strips to heat stress tests, it was found that the GIRARD'S Reagent T increased the heat stability of the enzymatic test strip even in the absence of TRIS glutamate from the test strip. In addition, if both the hydrazide and TRIS glutamate are omitted from the enzyme reagent composition, the enzymatic test strip showed essentially no enzymatic or chemical activity after being heat stressed at 60° C. for three days. Furthermore, enzymatic test strips including both the hydrazide and TRIS glutamate showed further improved test strip stability over test strips including only either the hydrazide or the TRIS glutamate. The hydrazide and amino acid derivative therefore were identified as components of the enzyme reagent composition that increase the thermal stability of enzymatic test strips used to assay liquid test samples for glucose.

TABLE II demonstrates that the addition of a hydrazide to an enzyme reagent composition including TRIS glutamate further improves the stability of dry phase enzymatic test strips, especially in assays for high glucose concentrations. TABLE II illustrates the results of urine glucose assays using a series of enzymatic test strips produced from enzyme reagent compositions of Example 3 that contain 25 mM or 0 mM, respectively, of the hydrazide, GIRARD'S Reagent T. These stabilized test strips were used to assay urine samples having standardized glucose concentrations in the range of from 30 mg/dL to 2000 mg/dL. From TABLE II, it is observed that the color block loss was less, therefore showing greater enzyme reagent composition stability, for enzymatic test strips including the hydrazide, GIRARD'S Reagent T. In addition, because the enzyme reagent composition of Example 3 includes the stabilizer TRIS glutamate, the results of TABLE II show further stabilization of the enzymatic test strip by incorporating both the hydrazide and the amino acid derivative, TRIS glutamate, as opposed to stabilizing the enzymatic test strip with only the amino acid derivative, TRIS glutamate.

TABLE II

| Color Block Loss Upon Adding a Hydrazide to a TRIS Glutamate-Containing Enzyme Reagent Composition | | | | | | |
|---|---|---|---|---|---|---|
| | Urine Glucose Concentration | | | | | |
| Amount of Hydrazide | 2000 mg/dL | 1000 mg/dL | 500 mg/dL | 250 mg/dL | 100 mg/dL | 30 mg/dL |
| 25 mM | 0.2 | 0.1 | 0.5 | 0.2 | 0.3 | 0.4 |
| 0 mM | 1.0 | 0.8 | 0.7 | 0.3 | 0.5 | 0.6 |

It should be noted that the values presented in TABLE II refer to the number of color blocks lost by the enzymatic test strip after a 3 day, 60° C. heat stress test compared to a control enzymatic test strip stored at room temperature in an assay for glucose in urine. The smaller the value of lost color blocks relates to a greater heat stability of the test strip. For example, assaying a urine sample containing 2000 mg/dL of glucose, gave a 1.0 block color loss for a heat stressed test strip including TRIS glutamate and absent GIRARD's Reagent T, compared to a non-heated stressed test strip, whereas a test strip including both GIRARD'S Reagent T and TRIS glutamate showed only a 0.2 color block loss. A test strip absent both the hydrazide and the amino acid derivative showed essentially no reactivity to the glucose concentration of the urine. Similarly improved results are observed throughout the glucose concentration range of 30 mg/dL through 2000 mg/dL.

It also has been found that by impregnating a carrier matrix with an enzyme reagent composition containing an amino acid or an amino acid derivative at a concentration of about 25 mM to about 200 mM, or with an enzyme reagent composition containing a hydrazide at a concentration of about 10 mM to about 50 mM not only sufficiently stabilizes and protects the resulting enzymatic test strip against heat, but also permits rapid rehydration of the dry phase test strip upon contact with the liquid test sample, thereby permitting a relatively rapid analyte assay. The rapid penetration of the test strip by the test sample and the rapid rehydration of the test strip permits full color development and resolution after only a relatively short time. Therefore, the assayer can examine the test strip relatively shortly after contact between the test strip and the test sample in order to determine the analyte concentration. Additionally, it has been found that at high TMB or other oxidizable indicator concentrations, such as from about 50 mM to about 100 mM in of the enzyme reagent composition, and at high TRIS glutamate concentrations, such as from about 100 mM to about 200 mM in the enzyme reagent composition, further enhances the stabilizing effect of the hydrazide.

To further show that the hydrazide or the amino acid or the amino acid derivative present in the enzyme reagent composition are the composition components that stabilize the enzymatic test strip, the enzyme reagent composition of Example 3, but absent the GANTREZ ES-225, was impregnated into a carrier matrix that was cut and made into test strips. In an enzymatic glucose assay, these test strips were compared to test strips having a carrier matrix impregnated with an enzyme reagent composition of Example 3 absent both the GANTREZ ES-225 and the hydrazide. After heat stressed storage at 60° C. for 3 days, the test strips including the hydrazide showed substantially greater activity towards glucose concentrations, and therefore were more heat stable, over the entire range of 30 mg/dL through 2000 mg/dL of glucose in urine. For example, in urine assays wherein the urine contains 1000 mg/dL or 2000 mg/dL of glucose, a test strip incorporating the enzyme reagent composition absent GANTREZ ES-225 and the hydrazide lost two color blocks, whereas a test strip incorporating the enzyme reagent composition absent only the GANTREZ ES-225 lost only one color block. Similarly, for assays on urine containing 100 mg/dL glucose, the respective color block losses were 0.8 and 0.5 color blocks.

The results of a similar test wherein the polyvinylpyrrolidone rather than the GANTREZ ES-225 was omitted from the enzyme reagent composition gave like results over the entire 30 mg/dL through 2000 mg/dL glucose concentration range. For example, a test strip incorporating an enzyme reagent composition absent the polyvinylpyrrolidone and the hydrazide showed a three color block loss in assaying urine samples containing 2000 mg/dL, 1000 mg/dL or 250 mg/dL of glucose, as opposed to a 1.2, 2.2 and 2 color block loss, respectively, for a test strip incorporating an enzyme reagent composition absent only the polyvinylpyrrolidone. It is well known that including the polyvinylpyrrolidone in the enzyme reagent composition reduces the overall reactivity of the test strips, so the absence of polyvinylpyrrolidone in the test strip shows a corresponding increase (greater color block loss) in test strip reactivity compared to test strips absent the GANTREZ ES-225. The results described above are summarized in TABLE III. Each test strip used in the assays illustrated in TABLE III also includes the stabilizer TRIS glutamate.

TABLE III

Stability of Test Strips Including a Hydrazide and an Amino Acid Derivative

| | Glucose Concentration | | | | | |
|---|---|---|---|---|---|---|
| | 2000 mg/dL | 1000 mg/dL | 500 mg/dL | 250 mg/dL | 100 mg/dL | 30 mg/dL |
| 1. No GANTREZ E-225 | 1 | 1 | 1 | 1 | 0.5 | 0.8 |
| 2. No GANTREZ E-225 & No Hydrazide | 2 | 2 | 1.8 | 1.2 | 0.8 | Death |
| 3. No Polyvinylpyrrolidone | 1.2 | 2.2 | 1.0 | 2 | 1.5 | 0.9 |
| 4. No polyvinylpyrrolidone & No Hydrazide | 3 | 3 | 1.5 | 3 | 1.5 | 1 |

(Values indicate loss in color blocks, i.e., 2 means 2 lost color blocks. The lower the number of lost color blocks, the greater the stability of the enzyme reagent composition and the enzymatic test strip.)

In the interpretation of TABLE III, it should be understood that the larger the number, the greater the loss in color blocks. Furthermore, a greater loss in color blocks indicates that the test strip has less of an ability to undergo a color change upon contacting glucose. In other words, the test strip is less reactive and hence is less stable. Therefore, from TABLE III, it can be seen that omitting either the GANTREZ ES-225 or the polyvinylpyrrolidone from the enzyme reagent composition, while still including the hydrazide, increases the stability of the enzymatic test strip.

In accordance with another important feature of the present invention, other amino acids, amino acid derivatives or hydrazides also can be used, either alone or in combination, to increase the stability of oxidase enzyme-based test strips. The preceding discussion has described the amino acid derivative TRIS glutamate and the hydrazide GIRARD'S Reagent T, either individually or in combination, as the stabilizer components of the enzyme reagent composition. However, several other amino acid or amino acid derivatives, particularly the amino acids lysine and arginine, have similarly improved the temperature stability of enzymatic test strips.

As previously described, European Patent No. 080,304 discloses the stabilizing effect of acidic amino acids, i.e., dicarboxylic acids of up to six carbon atoms that also include an amino moiety, on enzyme-containing reagent solutions. European Patent No. 080,304 does not teach or suggest the use of acidic amino acids as an enzyme stabilizer in a dry phase test strip. However, in accordance with an important feature of the present invention, it has been found that a variety of amino acids, especially the basic amino acids, such as monocarboxylic acids that include an amino moiety or a hydroxy moiety, like threonine, also improve the temperature stability of enzymatic test strips.

It has been theorized that the amino acids, amino acid derivatives or hydrazide compounds protect the test strip from chemical and enzymatic inactivation by two distinct mechanisms. One mechanism is direct stabilization of the oxidase enzyme and the other mechanism is protection of the enzyme from inactivation due to the mercury that is incorporated into the test strip to overcome ascorbate interference. However, a generalization of the precise mechanism that leads to enzyme stabilization, and therefore test strip stabilization, is mainly theoretical. For example, GIRARD'S Reagent T, a hydrazide derivative, has a different chemical structure from the amino acid and amino acid derivative compounds. However, similar to the amino acid and amino acid derivative compounds, the test strip stabilization mechanism afforded by the hydrazide can be rationalized as either a binding of a positively-charged moiety present in the stabilizer to the enzyme or the ability of the stabilizer to complex with mercuric oxide; or as a combination of both theories.

The manufacture of an enzyme-based glucose test strip usually includes two impregnation steps. The first impregnating solution is the enzyme reagent composition containing the oxidizable TMB dye and the enzymes. The second impregnating solution contains a mercury oxide-sarcosine complex. The second impregnation solution is used in the test strip solely to eliminate ascorbic acid interference. It is well known that incorporating the mercury-containing complex into the test strip usually causes a drastic drop in test strip reactivity. However, the principal function and benefit of the hydrazide, the amino acid or the amino acid derivative stabilizer, i.e., to protect the enzyme reagent composition from thermal inactivation, is observed in test strips prepared either including or excluding the mercury-containing complex.

The effectiveness of a particular stabilizer was evaluated by comparing the reactivity of the test strip containing the stabilizer to a control test strip. The control test strip included no stabilizers, however in the other test strips, a stabilizer, at concentrations ranging from 25 mM to 200 mM, was added to the enzyme reagent composition. The reactivity of the test strips was measured on a Rapid Scanner reflectance spectrophotometer. The reflectance, R, as taken from the reflectance scale of zero to one, was incorporated into the Kubelka-Munk function:

$$K/S = (1 - R^2/2R),$$

wherein K is the absorption coefficient, S is the scattering coefficient and R is reflectance. The reflectance values were determined at 540 nm (nanometers), then used for the calculation of K/S values. The K/S values are proportional to the test strip color, and therefore are proportional to test strip reactivity. Urine standards having glucose concentrations of negative, 30, 250 and 1000 mg/dL, respectively, were used to evaluate the stability of test strips containing the enzyme reagent composition. However, because the deactivation of the test strip reactivity was generally more observable, and more easily and accurately measured, when testing urine having a 1000 mg/dL glucose concentration, the K/S values determined from assaying a standardized urine containing 1000 mg/dL of glucose were used to calculate test strip reactivity, and hence test strip stability.

The stability of an enzymatic test strip can be expressed in two ways: (1) the relative reactivity, calculated as the activity ratio of a test strip impregnated with a stabilized enzyme reagent composition to a control test strip at room temperature, and (2) the % activity remaining, calculated as the % test strip activity remaining after a 3 day heat stress at 60° C. relative to the strip activity of an identical test strip after holding at room temperature for 3 days.

The enzymatic test strips used in this reactivity/stability study were prepared in the manner previously described by immersing the carrier matrix first in the stabilizer enzyme reagent composition of Example 4 and then, after drying, in the mercury-sarcosinate complex composition of Example 5.

EXAMPLE 4

Stabilized Enzyme Reagent Composition

| | |
|---|---|
| 3,3',5,5'-Tetramethylbenzidine (TMB) | 50 mM |
| Polyvinylpyrrolidone (45% aqueous) | 3% |
| Sodium Lauryl Sarcosinate (30% aqueous) | 0.3% |
| Dioctyl Sodium Sulfosuccinate | 0.2% |
| FD&C Yellow #5 Dye | 0.02% |
| Stabilizer | variable from 25 mM to 200 mM |
| Succinate Buffer | 250 mM |
| Glucose Oxidase | 90 U/mL |
| Peroxidase | 245 U/mL |
| Acetone Solvent | 40% final (by volume) |

EXAMPLE 5

Ascorbate Interference Composition

| | |
|---|---|
| Mercuric Oxide | 100 mM |
| Sarcosine | 400 mM |
| Polyvinylpyrrolidone (45% aqueous) | 4.4% |
| Dioctyl Sodium Sulfosuccinate | 0.06% |
| Isopropyl Alcohol | 15% final (by volume) |

Table IV shows the results of a stability study on enzymatic test strips impregnated with an enzyme reagent composition each including one of thirteen amino compounds or the hydrazide, GIRARD'S Reagent T, as a stabilizer for the enzyme reagent composition. The ability of the stabilizer to improve test strip heat stability is dependent on whether the test strip is impregnated with only the enzyme reagent composition or with both the enzyme reagent composition and the ascorbate interference composition. In some cases, the degree of improved stability imparted by the stabilizer is enhanced by incorporating the ascorbate interference composition into the test strip (i.e., GIRARD Reagent T); and in some cases the degree of improved stability imparted by the stabilizer is decreased by incorporating the ascorbate interference composition into the test strip (i.e., arginine). However, regardless of whether the test strip is impregnated with only the enzyme reagent composition, or with the enzyme reagent composition and the ascorbate interference composition, it has been found that including a stabilizer of the present invention in the enzyme reagent composition improves the heat stability of an enzymatic test strip.

TABLE IV

Effect of Stabilizers on the Reactivity of
Enzymatic Test Strips for Glucose
Without (A) or Including (B)
Ascorbate Interference Composition

|  |  | A. Enzyme Reagent Impregnation Only | | B. Enzyme Reagent and Ascorbate Impregnation | |
| --- | --- | --- | --- | --- | --- |
|  |  | Relative Reactivity | % Activity Remaining | Relative Reactivity | % Activity Remaining |
| Control | None | 1.00 | 28.5% | 0.06 | 0% |
| Arginine | 200 mM | 1.29 | 98.6% | 0.41 | 36.2% |
| Lysine | 100 mM | 0.66 | 81.0% | 0.85 | 69.1% |
| GIRARD Reagent T* | 50 mM | 0.70 | 93.3% | 0.35 | 97.1% |
| Histidine | 50 mM | 0.54 | 96.5% | 0.086 | 50.9% |
| Imidazole | 200 mM | 1.81 | 22.9% | 1.48 | 84.4% |
| TRIS-Glutamate | 200 mM | 1.52 | 68.6% | 0.91 | 45.2% |
| K-Glutamate | 200 mM | 1.25 | 71.4% | 0.32 | 75.2% |
| TRIS-Acetate | 200 mM | 1.64 | 33.8% | 0.46 | 32.1% |
| DL-$\beta$-Aminobutyric acid | 200 mM | 1.18 | 63.1% | 0.43 | 56.0% |
| $\gamma$-Aminobutyric acid | 200 mM | 1.75 | 62.0% | 0.26 | 104.0% |
| Threonine | 100 mM | 0.92 | 75.5% | 0.51 | 80.9% |
| Alanine | 140 mM | 1.59 | 59.2% | 0.36 | 72.5% |
| Glycine | 200 mM | 0.66 | 4.2% | 0 | 0 |
| Triethanolamine | 200 mM | 0.50 | 21.1% | 0 | 0 |

(*GIRARD'S Reagent T = (carboxymethyl)trimethylammonium chloride hydrazide)

The results tabulated in TABLE IV show that test strips impregnated only with the enzyme reagent composition and that included arginine, lysine, histidine or GIRARD'S T as the stabilizer, are the most stable test strips while glycine and triethanolamine are ineffective as stabilizers. The remaining compounds show various degrees of effectiveness as enzymatic test strip stabilizers. As discussed above, incorporating the ascorbate interference composition into the test strip may alter the degree of stabilization afforded by the stabilizer, but overall, except for glycine and triethanolamine, test strip heat stability is improved.

The data summarized in TABLE IV indicate that compounds having the following structural characteristics can be expected to impart heat stability and shelf life longevity to dry phase test strips impregnated with an enzyme reagent composition:

(1) An amino acid or amino acid derivative having a carbon chain of three or more and with a general structure $$X-CH_2-CH-COOH;$$
$$\phantom{X-CH_2-CH-}NH_2$$

(2) The amino acid or amino acid derivative having the general structure depicted in (1), wherein X is hydrogen, hydroxyl, imidazole or an alkyl group containing from one to four carbon atoms and having a positively charged moiety, such as the ammonium moiety in lysine or the guanidine moiety in arginine, or a carboxyl moiety, such as in glutamic acid;

(3) The presence of an $\alpha$-amino group is not always necessary, however both an amino moiety and a carboxyl moiety must be present in the compound;

(4) The presence of a negatively charged moiety in the —X group has not demonstrated any stabilizing or destabilizing effects on the enzymatic test strips; and (5) Imidazole does not have the model chemical structure of a compound expected to impart heat stability to an enzymatic test strip, but does impart heat stability, especially if the test strip also is impregnated with the ascorbate interference composition.

The effects of the ascorbate interference composition upon test strip stability is difficult to explain in view of the results tabulated in TABLE IV. The relative reactivity of test strips impregnated with both compositions varies from 0% to 148% of the control strip. The degree of reactivity of the test strip apparently correlates with the ability of the stabilizer compound to complex with mercury oxide. However, the stability of the test strip does not necessarily parallel the relative test strip reactivity, therefore suggesting that other mechanisms in addition to mercury complexation, by the stabilizer are involved. It should be noted that the stabilizers of the present invention also are able to protect the enzymes from thermal deactivation in addition to protecting the enzyme from mercury induced inactivation. In general it has been demonstrated that amino acids having a positively-charged moiety are effective stabilizers for dry phase enzymatic test strips.

Furthermore, GIRARD'S Reagent T, a hydrazide, has been found to be a very effective stabilizer for test strips impregnated with only the enzyme reagent composition and for test strips impregnated with the enzyme reagent composition and the ascorbate interference composition.

$$CH_3 \atop CH_3-N^+-CH_2-\overset{O}{\overset{\|}{C}}-NH-NH_2 \atop CH_3 \qquad\qquad I$$

The structure for GIRARD'S Reagent T, as depicted in structural formula I, differs from the proposed model chemical structure for the amino acid compounds that act as test strip stabilizers. Although the mechanism whereby GIRARD'S Reagent T stabilizes test strips is unclear, it is theorized that the positively charged ammonium moiety may bind directly to the enzyme and the carbazide moiety protects the enzyme from the mercury deactivation. In addition, because of its inherent reducing properties, the carbazide moiety may actually reduce the mercuric ion to metallic mercury.

Although the method and composition of the present invention described herein has principally related to assaying urine for glucose via a glucose oxidase/peroxidase reagent composition, the method and composition of the present invention also is useful to assay other liquid test samples, such as serum, for analytes other than glucose, such as cholesterol, uric acid or lower alcohols, by using the appropriate oxidase enzyme. Therefore, in accordance with an important feature of the present invention, the heat stability of dry phase enzymatic test strips, incorporating an oxidase enzyme reagent composition, is improved by including a hydrazide or an amino acid or an acid derivative in the oxidase enzyme reagent composition.

Obviously, many modifications and variations of the invention as hereinbefore set forth can be made without departing from the spirit and scope thereof and therefore only such limitations should be imposed as are indicated by the appended claims.

We claim:

1. A method of determining the presence or concentration of an analyte from the group consisting of glucose, cholesterol, uric acid and lower alcohols in a liquid sample to show the presence or concentration of the analyte being determined, said method comprising:
   (a) contacting the liquid sample with a reagent composition comprising an oxidase enzyme for the analyte being determined;
   an oxidizable chromogen;
   peroxidase;
   a buffer capable of buffering the reagent composition to a pH in the range of from about 4 to about 7; and
   a hydrazine selected from the group consisting of (carboxymethyl)trimethylammonium chloride hydrazine, 1-(carboxymethyl)pyridinium chloride hydrazine, 2-hydrazine-2-imidazoline-hydrobromide, 2-furonic acid hydrazine, hydrazine monohydrate and combinations thereof; and
   (b) determining the presence of concentration of the analyte in the liquid sample from the color change of the reagent composition.

2. A method of determining the presence or concentration of glucose in a liquid sample comprising:
   (a) contacting the liquid sample with a reagent composition comprising glucose oxidase; 3,3',5,5'-tetramethylbenzidine indicator dye; a peroxidase; a buffer capable of buffering the composition to a pH in the range of from about 4 to about 7; and from about 10 mM to about 50 mM of a hydrazide selected from the group consisting of (carboxymethyl)trimethylammonium chloride hydrazide, hydrazine, 1-(carboxymethyl)pyridinium chloride hydrazide, 2-hydrazine-2-imidazoline hydrobromide, 2-furonic acid hydrazide and combinations thereof; and
   (b) determining the presence or concentration of glucose in the liquid sample from the intensity and/or degree of color change of the reagent composition.

3. The method of claim 2 wherein the reagent composition further includes from about 25 mM to about 200 mM of the tris(hydroxymethyl)aminomethane salt of glutamic acid.

* * * * *

UNITED STATES PATENT AND TRADEMARK OFFICE
CERTIFICATE OF CORRECTION

PATENT NO. : 5,185,247
DATED : February 9, 1993
INVENTOR(S) : Ibrahim A. Ismail and Wen H. Wu It is certified that error appears in the above-identified patent and that said Letters Patent is hereby corrected as shown below:

Column 28, line 7, change "of" (first occurrence) to -- or --.

Abstract, line 14, change "sale" to --salt--.

Signed and Sealed this

Twenty-third Day of July, 1996

Attest:

BRUCE LEHMAN

Attesting Officer     Commissioner of Patents and Trademarks